United States Patent [19]

Wong

[11] 4,064,118

[45] Dec. 20, 1977

[54] BLOOD SUBSTITUTE BASED ON HEMOGLOBIN

[75] Inventor: Jeffrey Tze-Fei Wong, Don Mills, Canada

[73] Assignee: Hematech Inc., Toronto, Canada

[21] Appl. No.: 730,943

[22] Filed: Oct. 8, 1976

[30] Foreign Application Priority Data

Oct. 22, 1975 Canada .................................. 238305

[51] Int. Cl.$^2$ ....................... A23J 1/06; A61K 31/735
[52] U.S. Cl. ......................... 260/112.5 R; 260/112 B; 424/177
[58] Field of Search .................... 260/112.5 R, 112 R, 260/112 B; 424/177

[56] References Cited

U.S. PATENT DOCUMENTS

| 3,925,344 | 12/1975 | Mazur | 260/112.5 R |
|---|---|---|---|
| 4,001,200 | 1/1977 | Bonsen et al. | 260/112.5 R |
| 4,001,401 | 1/1977 | Bonsen et al. | 424/177 |

FOREIGN PATENT DOCUMENTS

| 736,354 | 9/1955 | United Kingdom. |
|---|---|---|
| 1,126,628 | 9/1968 | United Kingdom. |

OTHER PUBLICATIONS

Foerster et al., *Chemical Abstracts,* vol. 82:11,061q, (1975).

Kaplan et al., *Chemical Abstracts,* vol. 83:53,540w, (1975).

*Primary Examiner*—Walter C. Danison
*Attorney, Agent, or Firm*—Hirons & Rogers

[57] ABSTRACT

A blood substitute or blood extender is prepared by chemically coupling hemoglobin with a polysaccharide material selected from dextran and hydroxyethyl starch, and having a molecular weight of from about 5,000 to about 2,000,000, to form a covalently bonded chemical complex. The complex has similar oxygen transporting abilities to hemoglobin, and has a much lower rate of renal excretion.

14 Claims, 1 Drawing Figure

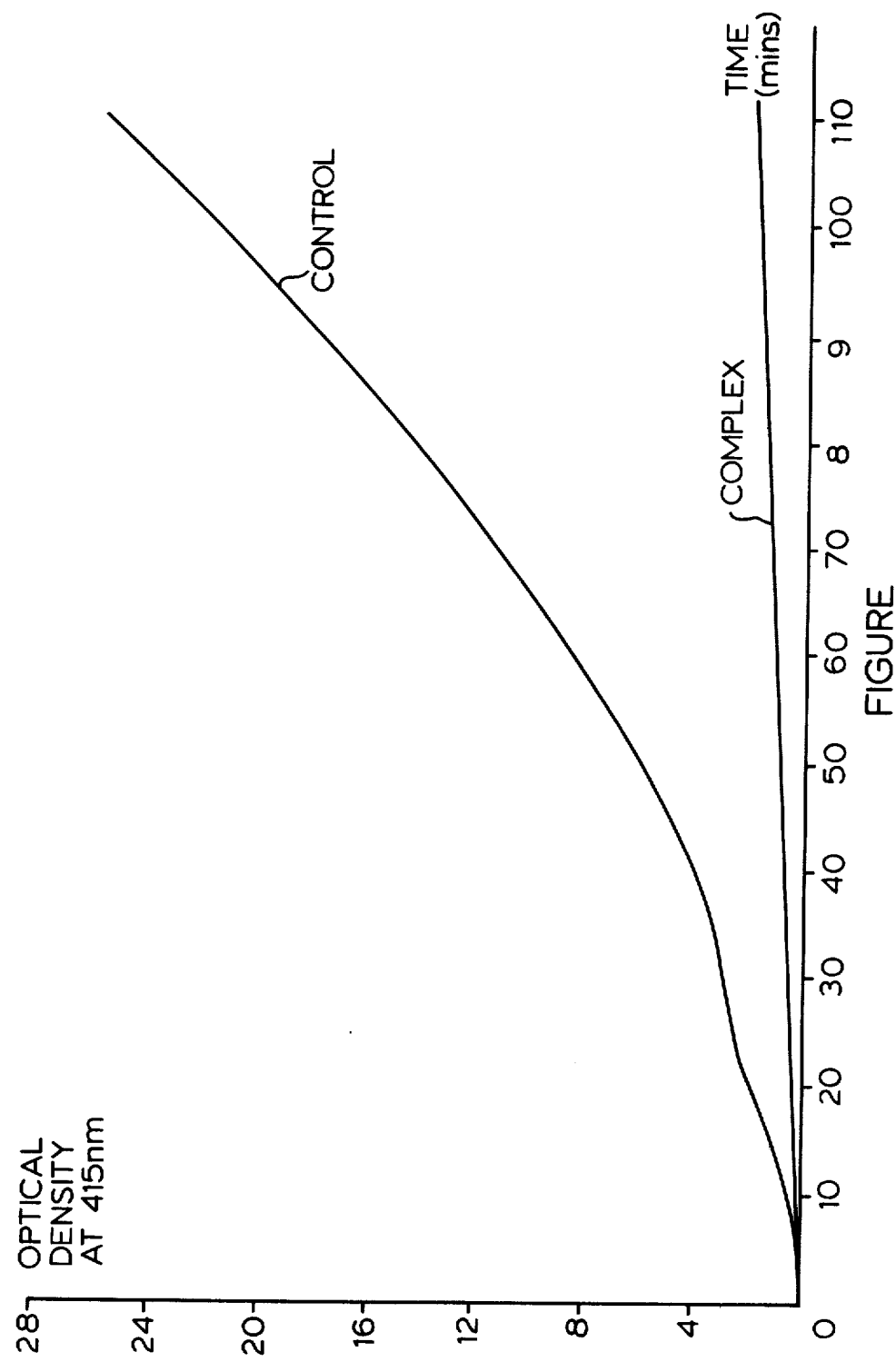

BLOOD SUBSTITUTE BASED ON HEMOGLOBIN

FIELD OF THE INVENTION

This invention relates to blood substitutes, and methods for their preparation. More particularly, it relates to a novel compound and composition which can be administered to human patients as a blood substitute by transfusion.

BACKGROUND OF THE INVENTION

It is a well known and well documented fact that the demand for blood supplies for administration to patients undergoing surgery and other emergency medical procedures has increased very rapidly over the past 30 years or so. The demand often exceeds the supplies available from human donors. Even larger volumes of blood would be used if it were readily available. Elective surgery is often postponed because of shortages of blood. Medical techniques continue to become more sophisticated and successful, so that the amounts of blood required continue to increase. Extracorporeal techniques require large quantities of blood, mostly for temporary use. There is therefore a need to develop blood substitutes, and to make the most efficient use of blood supplies which are available. This need exists not only in areas where advanced medical techniques are practiced, but also in underdeveloped areas of the world where expensive facilities for blood banking and blood typing are not available.

BRIEF DESCRIPTION OF THE PRIOR ART

A vital function of blood in the body is the delivery of oxygen to the cells and tissues of the body, so as to maintain the functions of the various body organs. Certain compounds such as dextran, hydroxyethyl starch, polyvinylpyrrolidone and gelatin have been proposed in the past for use as blood substitutes or plasma volume expanders. However, they do not possess the required ability to deliver oxygen and yield up the oxygen to the body tissues, so that they are not useful for the management of acute hemorrhage.

Two kinds of preparation have been proposed as oxygen carrying blood substitutes. Some perfluoro compounds such as perfluorotributylamine, perfluorodecalins and perfluorocyclic ethers can be prepared in the form of stable emulsions which have a high capacity for delivering oxygen. Whilst these compounds appear to be generally free from short term side effects on the body, other than incidences of lung lesions and thrombocytopenia, their possible long term toxicity is currently unknown. Also, the compounds are difficult to synthesize and purify.

The second kind of preparation is hemoglobin solution. Hemoglobin is well known to be a principal constituent of the red cells present in blood. It is a complex protein material containing molecules of iron. Its composition and structure has been extensively studied and reported in the literature. Its function in the animal body system is understood to be the transportation of oxygen to cells and tissues. Hemoglobin has the power of combining with oxygen easily and giving up the oxygen readily when the body requires it.

Use of hemoglobin solutions has the advantage, as compared with use of whole blood, that blood typing does not have to be undertaken. Such solutions therefore can be given to a patient in an emergency without taking the time to type and cross-match the blood. Blood types are understood to be determined by certain antigens present in the red cells of blood and certain natural antibodies present in the blood serum. Hemoglobin is not responsible for blood typing. Moreover, hemoglobin is a much easier material to store than whole blood, and does not deteriorate as quickly. Stocks of blood have to be discarded after a relatively short period of time. Hemoglobin can be isolated from blood and frozen so that it can be stored for much longer periods of time. Use of hemoglobin solution instead of whole blood thus has significant advantages, and tends to alleviate problems of lack of supply of whole blood, particularly lack of supply of blood of specific types.

However, hemoglobin is rapidly excreted from the kidney as urine from the sick patient. Frequent massive transfusions of hemoglobin solution must therefore be employed, and the high rate of excretion poses a potential hazard to patients with pre-existing renal disease. It has been reported that the half-disappearance time from the circulation, of hemoglobin administered as solution by transfusion, is only 1½ hours in monkeys.

SUMMARY OF THE INVENTION

It is an object of the present invention to provide a novel compound useful as a blood substitute or blood extender, for administration to human or animal patients.

It is a further object of the present invention to provide such a compound which is based upon hemoglobin.

It is a further object of the present invention to provide a process for preparing a blood substitute or blood extender by chemical treatment of hemoglobin.

The present invention provides a composition useful as a blood substitute or blood extender composition which comprises the water soluble product of chemically covalently coupling hemoglobin with a polysaccharide material selected from the group consisting of dextran and hydroxyethyl starch, said polysaccharide material having a molecular weight of from about 5,000 to about 2,000,000.

Also according to the present invention, there is provided a process of preparing a blood substitute or blood extender composition suitable for administration to an animal or human patient, which comprises chemically coupling hemoglobin with a polysaccharide material selected from dextran and hydroxyethyl starch, of a molecular weight from about 5,000 to about 2,000,000.

The problem of rapid excretion of hemoglobin when administered as a solution appears at least in part to be a consequence of its relatively low molecular weight. Hemoglobin has a molecular weight of the order of 65,000, which is apparently insufficiently high to permit its retention in the circulatory system for an adequate period of time, when it is supplied separately from red blood cells and plasma. The chemical product according to the present invention, however, has been found to have a sufficiently high molecular weight to allow its adequate retention in the body. In addition, the product according to the invention has reversible oxygen transportation capacity, allowing it to contribute to this important function of normal blood.

DESCRIPTION OF THE PREFERRED EMBODIMENTS

The preferred process for preparing the complex product according to the invention comprises the steps of first reacting the polysaccharide with a suitable chemical reagent to form a modified polysaccharide having on the polysaccharide molecule a chemical group capable of chemical interaction with groups on the hemoglobin. The polysaccharides used in the present invention, dextran and hydroxyethyl starch, have a plurality of hydroxyl groups in the molecule. Thus, a reagent is chosen to form the modified polysaccharide which is capable of reacting with the hydroxyl groups without of course deleteriously affecting the polysaccharide in other respects. Such reagents are well known in the art, and include those having chemical groups such as carboxylic acid anhydride, acyl halide, substituted alkyl halide and sulfate, cyanogen bromide, periodate, isocyanate, epichlorohydrin, etc.

These reagents used for preparing the modified polysaccharide should, in addition to the above mentioned chemical group for reacting with hydroxyl on the polysaccharide, be capable of putting onto the polysaccharide, groups capable of subsequent reaction with hemoglobin, or with some bridging compound capable of subsequent reaction with hemoglobin. As previously noted, hemoglobin is a complex protein material. Thus it has polypeptide chains containing the polypeptide linkage — CHR — CO — NH — R¹CH — derived from amino acid units. A fairly large variety of different amino acids are involved in the hemoglobin chains, and these amino acids provide chemical side groupings on the hemoglobin protein molecules which are available for chemical reaction with the modified polysaccharide.

Among such available groups on the hemoglobin are the following:
amino
phenolic
sulfhydryl
thiomethyl
imidazo
carboxyl
quanidine Thus there is used in the present invention a modified polysaccharide containing at least one chemical group capable of reacting with at least one of the aforementioned available groups on the hemoglobin molecule. Such suitable chemical groups on the modified polysaccharide are as follows:

acylating groups which react with the amino groups on the protein, for example acid anhydride groups, N-acylimidazole groups, acid azide groups, N-carboxy anhydride groups, diketene groups, dialkyl pyrocarbonate groups, imidoester groups, O-alkyl isourea groups, S-alkyl isourea groups, sulfonyl halide groups, sulfonate ester groups, and carbodiimide-activated carboxyl groups. All of the above groups are known to react with amino groups on proteins to form covalent bonds, involving acyl or similar linkages;

alkylating groups which react with sulfhydryl (mercapto), thiomethyl, imidazo or amino groups on the protein, such as halo-carboxyl groups, maleimide groups, activated vinyl groups, ethylenimine groups, aryl halide groups, 2-hydroxy5-nitro-benzyl bromide groups; and aliphatic aldehyde and ketone groups together with reducing agents, reacting with the amino group of the protein;

ester and amide forming groups which react with a carboxyl group of the protein, such as diazocarboxylate groups, and carbodiimide and amine groups together;

disulfide forming groups which react with the sulfhydryl groups on the protein, such as 5,5'-dithiobis (2-nitrobenzoate) groups and alkylmercaptan groups (which react with the sulfhydryl groups of the protein in the presence of oxidizing agents such as iodine);

dicarbonyl groups, such as cyclohexandione groups, and other 1,2-diketone groups, which react with the guanidino moieties of protein;

diazo groups, which react with phenolic groups on the protein molecule;

reactive groups from reaction of cyanogen bromide with the polysaccharide, which react with amino groups on the protein.

Thus, in summary, the complex according to the invention may be made by first modifying the polysaccharide chemically to produce a modified polysaccharide having at least one chemical group thereon which is capable of reacting with an available chemical group on the hemoglobin protein, and then reacting together the modified polysaccharide and the hemoglobin to form a covalently bonded complex thereof utilizing the chemical group reacted onto the modified polysaccharide. Reactions of the various groups referred to above which can be put on the polysaccharide with proteins are known in the art - see for example "Chemical Modification of Proteins" by Means & Feeney, published by Holden Day, 1971, and "Advances in Carbohydrate Chemistry and Biochemistry", Vol. 29, edited by R. S. Tipson and D. Horten, published by Academic Press, with chapter by Kennedy on polysaccharide derivatives.

It is preferred according to the invention to react the polysaccharide to produce a modified polysaccharide having groups which will react with the sulfhydryl groups of the hemoglobin. Particularly preferred groups are the halocarboxylate groups.

Specific examples of preferred synthetic methods for preparing the complex according to the invention are as follows:

Method I: React the polysaccharide (PS) initially with cyanogen bromide CNBr, which forms an activated intermediate which reacts with diaminoethane to form:

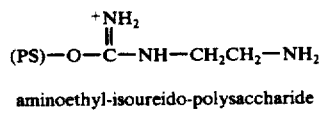

aminoethyl-isoureido-polysaccharide

The linkage between the ethyl group and dextran is most likely an isourea type linkage, although other types of chemical linkages are not completely ruled out. The aminoethyl-isoureidodextran so obtained is then acylated by bromoacetylbromide to yield bromoacetyl-aminoethyl-isoureido-polysaccharide:

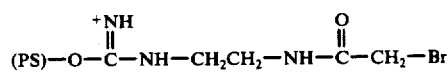

This in turn reacts with the sulfhydryl groups of hemoglobin (HB) to form hemoglobin-S-acetylaminoethyl-isoureido-polysaccharide:

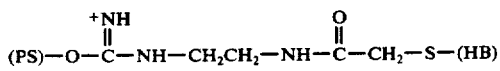

Method II: React the polysaccharide (PS) initially with 2-chloroethylamine to form aminoethyl-O-polysaccharide:

(PS)—O—CH$_2$CH$_2$—NH$_2$

Similar to Method I, successive reaction of this with bromoacetylbromide and hemoglobin (HB) yields hemoglobin-S-acetylaminoethyl-O-polysaccharide:

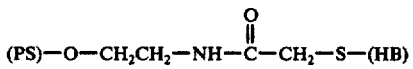
$$(PS)-O-CH_2CH_2-NH-\overset{\overset{O}{\|}}{C}-CH_2-S-(HB)$$

Method III: React the polysaccharide (PS) with sodium periodate to form the dialdehyde:

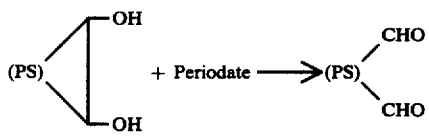

Reaction between the dialdehyde and the amino groups of hemoglobin (HB) yields hemoglobin-N-dextran:

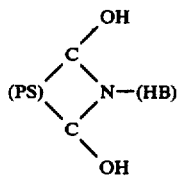

By proper adjustment of the conditions under which the modified polysaccharide is reacted with the hemoglobin, a yield of over 90% of coupled complex product can be obtained, rendering separation of the product from residual reactants unnecessary. For example, where the modified polysaccharide is N-bromoacetyl-aminoethylisoureido dextran (Br-dextran) prepared as described above, the concentrations of the hemoglobin and Br-dextran in the coupling reactant solution, and the reaction time, can be adjusted to give over 90% yields of coupled products. Too high a concentration of reactants leads to gelation of the reactant solution and formation of a cross linked product of excessively high molecular weight which is usually undesirable. It is preferred to use a molar ratio of Br-dextran to hemoglobin close to one, or less than one in the case where a dextran of high molecular weight is used. Formation of cross linked product can also be inhibited by lowering the pH to stop the alkylation reaction or by adding mercaptoethanol or cysteine to react with Br-dextran in competition with the hemoglobin sulfhydryls.

As previously noted, the polysaccharide used according to the present invention should have a molecular weight in the broad range from about 5,000 to about 2,000,000. The preferred molecular weight range, especially in the case of dextran, is from about 5,000 to about 200,000, and most preferably from about 20,000 to 70,000. Within such molecular weight ranges, coupling with hemoglobin takes place readily, and the reaction solutions have suitable viscosities for ease of handling. In addition dextrans of molecular weight below about 90,000 are known to be substantially non-allergenic, and are therefore desirable for use in the present invention.

The coupled product of the polysaccharide and hemoglobin may be a one to one coupling, or there may be several, e.g. up to 9, molecules of hemoglobin coupled to one molecule of polysaccharide. This can be controlled by the relative amounts of reactants in the coupling reaction, and control of other reaction conditions such as time, temperature and pH. The products of the present invention have molecular weights in the approximate range 70,000 to 2,000,000, and most preferably in the approximate range 85,000 to 135,000.

The hemoglobin-polysaccharide complex may be recovered in a physiologically acceptable carrier ready for administration to a patient. The reaction medium in which the complex is formed may constitute the carrier, provided it is physiologically acceptable.

REFERENCE TO THE DRAWING

The accompanying FIGURE illustrates graphically the results obtained according to Example 2, described below.

DESCRIPTION OF SPECIFIC PREFERRED EMBODIMENTS

Example 1 — Preparation of Dextran-Hemoglobin Complex 0.3 gm of cyanogen bromide is dissolved in 3 ml of acetonitrile and added to 100 ml of 2% dextran solution (mol. wt. 200,000). The pH is maintained at 10.8 with 1 M NaOH for 5 minutes. 2 ml of diaminoethane is then added. The pH is adjusted to 9.5 with concentrated HCl, and the reaction mixture is left overnight.

The mixture is dialysed thoroughly against distilled water and freeze-dried. The freeze-dried aminated dextran can be stored for a long time.

All the activated dextran recovered (1.6 — 1.7 gm) is dissolved in 50 ml 0.1 phosphate buffer, pH 7.0, and 2 ml of bromoacetyl-bromide is very slowly added, with vigorous stirring, over a period of 2 hrs. The pH is constantly maintained at 7.0 with the addition of 1M NaOH. When the reaction is over, the mixture is dialysed thoroughly against distilled water and then freeze-dried. 1.4 gm of brominated dextran, or Br-dextran is recovered.

1 gm of Br-dextran is added to 30 ml of a 2 - 3% solution of human hemoglobin in 0.1M sodium bicarbonate buffer, pH 9.5, and the reaction is allowed to go overnight.

Dextran-hemoglobin and free hemoglobin are separated from each other on a Sephadex G-200 column. Yield of dextranhemoglobin is 70 - 80% of the total hemoglobin added.

Example 2 — Renal Excretion of Hemoglobin and Dextran-Hemoglobin by Rats

To test the effectiveness of the complex according to the present invention as a blood substitute, 3 ml of a 2% dextran-hemoglobin complex solution, prepared according to Example 1, was infused into a Wistar rat, and the amount of dextran-hemoglobin excreted by the animal was estimated by washing the bladder with a continuous stream of physiological saline, and measuring the amount of dissolved hemoglobin in the wash as a function of time. An exactly similar control experiment was run, except using 3 ml of a 2% hemoglobin solution. In both instances, the hemoglobin content was determined spectrophotometrically in terms of optical density at 415 nm.

The results are shown graphically on the attached Figure. This is a graphical representation of optical density plotted against time, for the respective experiments. It will be seen that the rate of excretion of the hemoglobin is much greater than the rate of excretion of the dextran-hemoglobin complex.

This experiment demonstrates that dextran-hemoglobin is potentially a much more useful blood substitute than free hemoglobin with respect to its vastly improved retention by the animal against renal excretion.

globin solution (containing 2.5, 5 or 10% hemoglobin in 0.1M sodium bicarbonate, pH 9.5). The coupling was allowed to proceed with constant mixing at 4° C. Yields of coupled products were determined by eluting the reaction mixture on a Sephadex column with 0.05M phosphate buffer, Ph 7.5. Hemoglobin content was determined by absorbance at specified wavelengths. Results are given in Table 1.

TABLE I

| Dextran M. Wt. | %Br-Dextran in Reactant Sol" | % Hemoglobin in Reactant Sol" | Molar Ratio of Dextran/ Hemoglobin | Reactin Time (Hrs.) | Viscosity (Centi Stokes) | % Yield of Coupled Product |
|---|---|---|---|---|---|---|
| 200,000 | 3.33 | 5.0 | 0.21 | 24 | 35.19 | 96 |
| 200,000 | 3.33 | 5.0 | 0.21 | 48 | gelled | |
| 200,000 | 3.33 | 2.5 | 0.43 | 24 | 9.86 | 97 |
| 200,000 | 1.66 | 5.0 | 0.11 | 24 | 7.56 | 92 |
| 200,000 | 1.66 | 5.0 | 0.11 | 48 | 8.47 | 96 |
| 110,000 | 3.33 | 5.0 | 0.39 | 24 | 20.94 | 95 |
| 110,000 | 3.33 | 5.0 | 0.39 | 48 | 45.29 | 97 |
| 110,000 | 3.33 | 5.0 | 0.39 | 72 | gelled | |
| 110,000 | 3.33 | 2.5 | 0.78 | 24 | 7.43 | 97 |
| 110,000 | 1.66 | 5.0 | 0.19 | 24 | 6.43 | 85 |
| 110,000 | 1.66 | 5.0 | 0.19 | 48 | 7.39 | 93 |
| 110,000 | 1.66 | 5.0 | 0.19 | 72 | 8.07 | 95 |
| 70,000 | 3.33 | 5.0 | 0.61 | 24 | 19.40 | 99 |
| 70,000 | 3.33 | 2.5 | 1.22 | 24 | 6.72 | 98 |
| 70,000 | 1.66 | 5.0 | 0.31 | 24 | 5.81 | 87 |
| 70,000 | 1.66 | 5.0 | 0.31 | 48 | 6.49 | 94 |
| 70,000 | 1.66 | 5.0 | 0.31 | 72 | 6.90 | 96 |
| 40,000 | 3.33 | 10.0 | 0.54 | 24 | 15.37 | 83 |
| 40,000 | 3.33 | 10.0 | 0.54 | 48 | 20.10 | 90 |
| 40,000 | 3.33 | 10.0 | 0.54 | 72 | 22.65 | 94 |
| 40,000 | 3.33 | 5.0 | 1.07 | 24 | 6.32 | 96 |
| 40,000 | 3.33 | 2.5 | 2.15 | 24 | 4.14 | 99 |
| 40,000 | 1.66 | 5.0 | 0.54 | 72 | 4.29 | 92 |
| 20,000 | 3.33 | 10.0 | 1.07 | 48 | 8.91 | 97 |
| 20,000 | 3.33 | 10.0 | 1.07 | 72 | 10.24 | 98 |
| 20,000 | 1.66 | 5.0 | 1.07 | 72 | 3.07 | 94 |

EXAMPLE 3

2 g of dextran of weight average molecular weight 110,000 was dissolved in 75 ml distilled water, the pH was adjusted to 10.8 with 2M NaOH, and to this 0.3 g cyanogen bromide dissolved in 3 ml of acetonitrile was added with stirring at room temperature. The pH was maintained at 10.8 for 5 minutes by addition of 2M NaOH. The pH was then adjusted to about 2.0 – 2.5 with concentrated HCl and the solution was stirred for another minute. 3 ml of diaminoethane was added along with additional HCl to prevent the pH from exceeding 9.5; the final pH was adjusted to 9.5. The solution was stirred overnight at 4°. The aminated dextran formed was dialyzed in a Bio-Fiber 50 beaker (Bio-Rad Laboratories) against deionized water until no free amine could be detected in the dialysate by ninhydrin. The dialyzed solution was lyophilized to give about 1.6 g of dried aminated dextran. This was dissolved in 50 ml 0.1M phosphate buffer, pH 7.0, and 3 ml of bromoacetyl bromide was added through a pasteur pipette with a finely drawn capillary tip over a period of 60 minutes. Throughout the solution was stirred vigorously in an ice-water bath, and maintained at pH 6.6 to 6.8 by means of a pH-stat with the addition of 2M naOH solution during the addition of bromoacetyl bromide. Afterwards the solution was dialyzed against deionized water until no free bromine could be detected in the dialysate by silver nitrate. About 1.5 g of Br-dextran was obtained upon lyophilization. The experiment was repeated using other dextrans of average molecular weight 200,000; 70,000; 40,000; and 20,000. The bromine content of the various Br-dextrans synthesized, determined on the basis of elemental analysis, was in the range 9 – 11 glucose residues per bromine atom.

The Br-dextran so formed were coupled with hemoglobin, by dissolving a specified amount in 6 ml hemo- These results show that with each dextran over 90% yields of coupled product can be obtained by suitable choice of experimental conditions.

Example 4 — Preparation of Dextran-Hemoglobin Complex by Method II

One gm of dextran (mol. wt. 40,000) was thoroughly mixed with 1 ml of chloroethylamine, which was obtained as the upper phase from an addition of concentrated NaOH to chloroethylamine hydrochloride. The mixture was further mixed with 0.4 ml. of concentrated NaOH, placed in a capped tube and autoclaved at 120° C for 1 hour. Then 1 ml of chloroethylamine and 0.4 ml of concentrated NaOH was added, and the mixture again autoclaved at 120° for 1 hour; this was repeated yet another time. After cooling, the mixture was thoroughly dialysed against distilled water and placed finally in 11 ml of 0.1 M phosphate buffer, pH 6.8.

This solution of aminoethyl-O-dextran was acylated with the slow addition of 0.5 ml of bromoacetylbromide over a period of about 1 hour. It was thoroughly dialysed against distilled water and freeze-dried.

0.1 gm of the freeze dried bromoacetyl-aminoethyl-O-dextran was added to 1.7 ml of 5% human hemoglobin in 0.1 M Sodium bicarbonate buffer, pH 9.5, and held at 4° C for 48 hours. Chromatography of Sephadex indicated that over 90% of the hemoglobin was coupled in the form of dextran-hemoglobin.

Example 5 — Preparation of Dextran-Hemoglobin Complex by Method III

One milliliter of a 12% aqueous solution of sodium periodate was added to 10 ml of a 10% aqueous solution of dextran, and the mixture was left overnight in the dark at 4° C. A 3% solution of sodium bisulfite was added until the mixture turned brown and then, once again, colourless. The mixture was dialyzed against distilled water to yield the dextran dialdehyde solution. It was then added to 2 volumes of 3% stroma-free hemoglobin in 0.3 M sodium bicarbonate buffer, pH 9.5. Coupling of hemoglobin to dextran was allowed to proceed overnight at 4° C. The dextran-hemoglobin complex formed was separated from uncoupled hemoglobin by means of chromatography on a Sephadex G-200 column. About 60% yield of coupled product was obtained.

Example 6 — Renel Excretion of Hemoglobin and Dextran-Hemoglobin by Rabbits

Male rabbits, of body weight 3.3–3.5 kg, were anesthetized with 0.1 g of sodium pentothal. A solution of hemoglobin or dextran-hemoglobin (molecular weight of dextran: 200,000 – 275,000) according to the invention, in a standard kidney dialyzing buffer (according to Rabiner et al, 1967, J. Exp. Med. 126, 1127–1142), containing 20$\mu$Ci (microCuries) of [$^3$H] methoxy-inulin, was infused into each animal through the marginal ear vein at 1.1 ml/minute. After the solution had been infused, infusion was continued at the same rate with the buffer to maintain urinary output. At intervals, the content of the bladder was washed out with three 5-ml portions of 0.9% saline with the use of a Foley no. 8 catheter (3 ml) and, after centrifugation at 3000 $\times$ g for 10 minutes to remove any sedimentable material, the dissolved hemoglobin or dextranhemoglobin in the combined washes was determined on the basis of absorbance at 576 nm. The [$^3$H] inulin content in the combined washes was measured by scintillation counting with correction for quenching by hemoglobin; an external radiation standard in the Nuclear Chicago Mark II counter was used to determine quenching. Plasma concentration of hemoglobin or dextran-hemoglobin was determined at various times by withdrawing blood samples from the carotid artery and making absorbance measurements on the samples at 576 nm after sedimenting the erythrocytes.

Tests were conducted using 50 ml or 30 ml samples of 1% hemoglobin, or dextran-hemoglobin containing 1% equivalent of hemoglobin.

It was found that the dextran-hemoglobin, specifically that produced by the method of examples 1 and 3, was excreted through the kidneys and removed from circulation at a greatly reduced rate compared to free hemoglobin even though renal function in the animals infused with dextran-hemoglobin, as indicated by inulin excretion, was unimpaired. Furthermore, since it was repeatedly observed with different animals and at different dosages of infusion, this dissimilar physiological behaviour of dextran-hemoglobin and free hemoglobin was due to the different nature of the substances, not to some chance variation in, for example, the blood haptoglobin level of the experimental animals.

The oxygen binding characteristics of products according to the present invention are determined by the method of Benesch et al, (1965) Anal. Biochem. 11, 81–87. It is found that, as compared with hemoglobin, the products according to the present invention tend to show a somewhat greater affinity for oxygen, but retain the essential oxygen transporting and releasing capability of hemoglobin. As measured by the half-saturation oxygen tension, the dextranhemoglobin complex prepared by method I described above shows approximately 2.5-fold greater affinity for oxygen compared to free hemoglobin. The oxygen affinity of the complex can be varied by suitable chemical treatment of the hemoglobin, before or after coupling with the polysaccharide, for example by reacting it with pyridoxal phosphate and reducing with sodium borohydride.

I claim:

1. A composition useful as a blood substitute or blood extender for administration to human or animal patients, said composition comprising the water soluble high molecular weight product of covalently coupling hemoglobin and a modified polysaccharide having a molecular weight of from about 5,000 to about 2,000,000, the modified polysaccharide being selected from the group consisting of dextran and hydroxyethyl starch modified to contain chemical groups capable of reaction with the chemical side groupings on the hemoglobin, said chemical side groupings being selected from the group consisting of amino, phenolic, sulfhydryl, thiomethyl, imidazo and carboxyl groupings.

2. The composition of claim 1 wherein the polysaccharide has a molecular weight of from about 5,000 to about 200,000.

3. The composition of claim 1 wherein the polysaccharide has a molecular weight of from about 20,000 to about 70,000.

4. The composition of claim 1 wherein the polysaccharide is dextran.

5. The composition of claim 4 which comprises the product of reacting hemoglobin with dextran modified to contain at least one chemical group reactive with a side grouping on the homoglobin and selected from the group consisting of acylating groups; alkylating groups; ester and amide forming groups; and disulfid forming groups.

6. The composition of claim 4 which comprises the product of reacting hemoglobin with dextran modified to contain at least one chemical group selected from the group consisting of dicarbonyl groups, diazo groups, and reactive groups from reaction of cyanogen bromide with the dextran.

7. The composition of claim 1 comprising the high molecular weight product of reacting bromoacetyl-aminoethyl-isoureido-polysaccharide with hemoglobin.

8. The composition of claim 1 comprising the high molecular weight product of reacting bromoacetyl-aminoethyl-O-polysaccharide with hemoglobin.

9. The composition of claim 1 comprising the high molecular weight product of reacting dialdehyde polysaccharide with hemoglobin.

10. A process for preparing a composition useful as a blood substitute or blood extender, which comprises:
   a. chemically modifying a polysaccharide of approximate molecular weight 5,000 – 2,000,000 and selected from the group consisting of dextran and hydroxyethyl starch, to introduce into said polysaccharide chemical groups capable of reaction with hemoglobin and selected from acylating groups, alkylating groups, ester forming groups, amide forming groups and disulfide forming groups;
   b. reacting the high molecular weight product of step (a) with hemoglobin, to form a water soluble covalently coupled complex thereof;
   the polysaccharide being selected from the group consisting of dextran and hydroxyethyl starch.

11. The process of claim 10 which comprises the steps of:

a. reacting the dextran or hydroxyethyl starch with cyanogen bromide;
b. reacting the high molecular weight product of step (a) with diaminoethane;
c. acylating the high molecular weight product of step (b) with a haloacetylhalide;
d. reacting the high molecular weight product of step (c) with hemoglobin.

12. The process of claim 10 which comprises the steps of:
a. reacting the dextran or hydroxyethyl starch with a 2-haloethylamine;
b. reacting the high molecular weight product of step (a) with a haloacetylhalide;
c. reacting the high molecular weight product of step (b) with hemoglobin.

13. A macromolecular water soluble compound having oxygen transporting capability and useful in blood substitute or blood extender composition, having an approximate molecular weight of from about 70,000 to about 2,000,000, and having the general formula (PS) — X — (HB), where
(PS) represents a polysaccharide of molecular weight from about 5,000 to about 2,000,000 and selected from the group consisting of dextran and hydroxyethyl starch;
X represents a covalently bonded chemical bridging group and
HB represents hemoglobin.

14. The compound of claim 13, which is selected from the group consisting of hemoglobin-S-acetylaminoethyl-isoureido-polysaccharide; Hemoglobin-S-acetylaminoethyl-O-polysaccharide; and hemoglobin-N-dextran.